(12) United States Patent
Alon

(10) Patent No.: US 9,766,317 B2
(45) Date of Patent: Sep. 19, 2017

(54) APPARATUS, SYSTEMS AND METHODS WHICH ARE BASED ON MAGNETIC RESONANCE IMAGING FOR EVALUATION(S) OF RADIO FREQUENCY EMITTING DEVICE(S)

(71) Applicant: NEW YORK UNIVERSITY, New York, NY (US)

(72) Inventor: Leeor Alon, New York, NY (US)

(73) Assignee: New York University, New York, NY (US)

(*) Notice: Subject to any disclaimer, the term of this patent is extended or adjusted under 35 U.S.C. 154(b) by 674 days.

(21) Appl. No.: 14/354,396

(22) PCT Filed: Oct. 25, 2012

(86) PCT No.: PCT/US2012/061969
§ 371 (c)(1),
(2) Date: Apr. 25, 2014

(87) PCT Pub. No.: WO2013/063302
PCT Pub. Date: May 2, 2013

(65) Prior Publication Data
US 2014/0340084 A1    Nov. 20, 2014

Related U.S. Application Data

(60) Provisional application No. 61/551,354, filed on Oct. 25, 2011.

(51) Int. Cl.
*G01R 35/00* (2006.01)
*G01R 33/48* (2006.01)
(Continued)

(52) U.S. Cl.
CPC ............... *G01R 35/00* (2013.01); *A61B 5/01* (2013.01); *A61B 5/055* (2013.01); *G01R 33/4828* (2013.01)

(58) Field of Classification Search
CPC .......... G01R 35/00; G01R 33/48; A61B 5/01; A61B 5/055
See application file for complete search history.

(56) References Cited

U.S. PATENT DOCUMENTS 7,246,939 B1    7/2007 Gultekin
2003/0069497 A1*    4/2003 Ochi ............... A61B 5/055
600/422

(Continued)

FOREIGN PATENT DOCUMENTS

WO    WO 2008/028497    8/2008

OTHER PUBLICATIONS

International Search Report for International Patent Application No. PCT/US2012/061969 dated Feb. 14, 2013.
(Continued)

*Primary Examiner* — Rodney Bonnette
(74) *Attorney, Agent, or Firm* — Andrews Kurth Kenyon LLP

(57) ABSTRACT

Exemplary system, method and computer accessible medium can be provided for evaluating at least one radio frequency transmitting arrangement. For example, it is possible to receive a first information associated with at least one scan of at least one live subject corresponding to one or more effects of the transmitting arrangement(s) on the at least one live subject, and determine a second information based on the first information.

29 Claims, 4 Drawing Sheets

(51) Int. Cl.
   A61B 5/01    (2006.01)
   A61B 5/055   (2006.01)

(56) References Cited

U.S. PATENT DOCUMENTS

| | | | |
|---|---|---|---|
| 2004/0056103 A1* | 3/2004 | Sepponen | A61B 5/04282 235/487 |
| 2010/0013481 A1* | 1/2010 | Hirata | A61B 5/055 324/309 |
| 2010/0125438 A1 | 5/2010 | Audet | |
| 2010/0238362 A1* | 9/2010 | Hughes | H04N 5/64 348/738 |
| 2011/0257509 A1 | 10/2011 | Olsen et al. | |
| 2011/0306870 A1* | 12/2011 | Kuhn | A61N 1/406 600/411 |

OTHER PUBLICATIONS

Written Opinion for International Patent Application No. PCT/US2012/061969 dated Feb. 14, 2013.
David H. Gultekin et al. "NMR Imaging of Cell Phone Radiation Absorption in Brain Tissue," PNAS Early Edition, www.pnas.org/cgi/doi/10.1073/pnas.1205598109, pp. 1-6.
Wikipedia Mobile phone http://en.wikipedia.org/wiki/Mobile_phone_radiation_and_health.
ICNIRP, "Exposure to high frequency electromagnetic fields, biological effects and health consequences" (100 kHz-300 GHz). (2009).
Cardis, "Brain tumour risk in relation to mobile telephone use: results of the Interphone international case-control study," Int. J. Epidemiol, vol. 39, p. 675 (2010).
Khurana, V.G. et al., "Cell phones and brain tumors: a review including the long-term epidemiologic data," Surg. Neurol, vol. 72, p. 205 (2009).
Borbely, A. A. et al., "Pulsed high-frequency electromagnetic field affects human sleep and sleep electroencephalogram," Neurosci. Lett., vol. 275, p. 207 (1999).
Croft, R. J. et al., "The effect of mobile phone electromagnetic fields on the alpha rhythm of human electroencephalogram," Bioelectromagnetics, vol. 29, p. 1 (2008).
Huber, R. et al., "Radio frequency electromagnetic field exposure in humans: estimation of SAR distribution . . . and heart rate," Bioelectromagnetics vol. 24, p. 262 (2003).
Loughran, S. P. et al., "The effect of electromagnetic fields emitted by mobile phones on human sleep," Neuroreport, vol. 16, p. 1973 (2005).
Luria, R. et al., "Cognitive effects of radiation emitted by cellular phones: the influence of exposure side and time," Bioelectromagnetics, vol. 30, p. 198 (2009).
Regal, S.J. et al., "Pulsed radio frequency radiation affects cognitive performance and the waking electroencephalogram," Neuroreport, vol. 18, p. 803 (2007).
Regel, S.J. et al., "Pulsed radio-frequency electromagnetic fields: dose-dependent effects on sleep, the sleep EEG & cognitive performance," J. Sleep Res. vol. 16, p. 253 2007.
Crespo-Valero, P. et al., "Novel methodology to characterize electromagnetic exposure of the brain," Physics in Medicine and Biology, vol. 56, pp. 383-396 (2011).
Bicher, H. I., "The physiological effects of hyperthermia," Radiology, vol. 137, pp. 511-513 (1980).
Ishihara, Y. et al., "A precise and fast temperature mapping using water proton chemical shift," Magn Reson Med, vol. 34, pp. 814-823 (1995).
De Poorter, J., "Noninvasive MRI thermometry with the proton resonance frequency method: study of susceptibility effects," Magn Reson Med, vol. 34, pp. 359-367 (1995).
Rieke, V. et al., "Referenceless MR thermometry for monitoring thermal ablation in the prostate," IEEE Trans Med Imaging, vol. 26, pp. 813-821 (2007).
Hekmatyar, S. K. et al., "Noninvasive MR thermometry using paramagnetic lanthanide complexes . . . acid (DOTMA4-)," Magnetic resonance in medicine, vol. 53, pp. 294-303 (2005).
Kosowsky, A., et al., "Cell phone activation and brain glucose metabolism," JAMA, vol. 305, pp. 2066; 2067-2068 (2011).
Lai, H et al., "Cell phone radiofrequency radiation exposure and brain glucose metabolism," Journal of the American Medical Association, vol. 305, pp. 828-829 (2011).
Volkow, N. D. et al., "Effects of cell phone radiofrequency signal exposure on brain glucose metabolism," JAMA vol. 305, pp. 808-813, (2011).
"Is there a link between cell phone use and cancer?," Mayo Clinic Womens Healthsource vol. 15, p. 8. (2011).
Christ, A., "The Virtual Family—development of surface-based anatomical models of two adults & two children for dosimetric simulation," Phys. Med. Biol. vol. 55, p. N23 (2010).
Ahlbohm, A. et al., "Epidemiologic evidence on mobile phones and tumor risk: a review," Epidemiology vol. 20, p. 639 (2009).
Anderson, V. et al., "Measurements of skin surface temperature during mobile phone use," Bioelectromagnetics vol. 28, pp. 159-162, (2007).
Beard, B. et al., "Comparisons of computed mobile phone . . . phantom to that in anatomically correct models of the human head," IEEE Trans. Electromagn. vol. 48, p. 397 (2006).
Blackman, C., "Cell phone radiation: Evidence from ELF and RF studies supporting more inclusive risk identification & assessment," Pathophysiology vol. 16, pp. 205-216, (2009).
Lehrer, S et al., Association between number of cell phone contracts and brain tumor incidence in Nineteen U.S. States, J Neurooncol., vol. 101, pp. 505-507. (2011).
Cardis, E. et al., "Risk of brain tumours in relation to estimated RF dose from mobile phones: results from five Interphone countries," Occup Environ Med, (2011).
Cardis, E. et al., "Estimation of RF energy absorbed in the brain from mobile phones in the Interphone Study," Occup Environ Med, 2011 (2011).
Chavdoula, E. D. et al., "Comparison of biological effects between . . . mobile phone radiation: Detection of apoptotic cell-death features," Mutat Res vol. 700, pp. 51-61, (2010).
Christ, A. et al., "Age dependent tissue-specific exposure of cell phone users," Phys. Med. Biol vol. 55, p. 1767 (2010).
Dendy, P. P., "Mobile phones and the illusory pursuit of safety," Lancet vol. 356, pp. 1782-1783, (2000).
Gabriel, S. et al., "The dielectric properties of biological tissues: III. Parametric models for the dielectric spectrum of tissues," Phys. Med. Biol. vol. 41, p. 2271 (1996).
Hamblin, D. L. et al., "EEG electrode caps can reduce SAR induced in the head by GSM900 mobile phones," IEEE Trans Biomed Eng vol. 54, pp. 914-920 (2007).
Hu, Q, et al., "Fast, accurate, and automatic extraction of the modified talairach cortical landmarks from magnetic resonance images," Magn. Reson. Med. vol. 53, p. 970 (2005).
Kainz, W et al., "Dosimetric comparison of the specific . . . head models using a novel definition for the mobile phone positioning," Phys. Med. Biol vol. 50, p. 3423 (2005).
Kheifets, L et al., "The sensitivity of children to electromagnetic fields," Pediatrics vol. 116, p. 303 (2005).
Alon, L., "Local SAR Calibration and Prediction Model in Parallel Transmit," MRI. ISMRM (2010).
Kivekas, O. et al., "Bandwidth, SAR, and efficiency of internal mobile phone antennas," Electromagnetic Compatibility, IEEE Transactions on vol. 46, pp. 71-86 (2004).
Kumar, N.R. et al., "Exposure to cell phone radiations produces biochemical changes in worker honey bees," Toxicol Int vol. 18, pp. 70-72, (2011).
Lancaster, J L et al., "Automated labeling of the human brain: a preliminary . . . development and evaluation of a forward-transform method," Hum. Brain Mapp vol. 5 p. 238, (1997).
Lancaster, J L et al., "Automated Talairach atlas labels for functional brain mapping," Hum. Brain Mapp. vol. 10, p. 120 (2000).
Lonn, S. et al., "Output power levels from mobile phones in different geographical areas; implications for exposure assessment," Occup Environ Med vol. 61, pp. 769-772, (2004).

(56) References Cited

OTHER PUBLICATIONS

Wake K., et al., "Estimation of 3D SAR distributions from mobile phone compliance . . . local exposure assessment in epidemiological study," Proc. 28th URSI General Assembly (2005).
Mailankot, M. et al., "Radio frequency electromagnetic . . . phones induces oxidative stress and reduces sperm motility in rats," Clinics (Sao Paulo) vol. 64, pp. 561-565, (2009).
Marino, A. A. et al., "Nonlinear changes in brain electrical activity due to cell phone radiation," Bioelectromagnetics vol. 24, 339-346, (2003).
McIntosh, R. L. et al., "Assessment of SAR and thermal changes near a cochlear implant system for mobile phone type exposures," Bioelectromagnetics vol. 29, pp. 71-80, (2008).
Gosselin, M.C. et al., Effects of heterogeneous tissue distribution . . . phones: influence on epidemiologic studies, Proc. 32nd Annu. Mtg of the Bioelectromag. Society (2010).
Nordstrom, C.H., "Cell phone activation and brain glucose metabolism," JAMA vol. 305, p. 2067; (2011).
Parkar, M.A. et al., "Effect of cell phone exposure on physiologic and hematologic parameters . . . profile," Jour of basic and clinical physiol and pharma vol. 21, pp. 201-210 (2010).
Peres, J., "Who Classification Sparks Debate Over Cell Phone Safety," Journal of the National Cancer Institute vol. 103, pp. 1146-1147, (2011).

\* cited by examiner

APPARATUS, SYSTEMS AND METHODS WHICH ARE BASED ON MAGNETIC RESONANCE IMAGING FOR EVALUATION(S) OF RADIO FREQUENCY EMITTING DEVICE(S)

CROSS REFERENCE TO RELATED APPLICATION(S)

This present application relates to and claims the benefit and priority from International Patent Application No. PCT/US2012/061969 filed on Oct. 25, 2012, pursuant to 35 U.S.C. §119(e) from U.S. Provisional Patent Application Serial No. 61/551,354 filed on Oct. 25, 2011, the entire disclosures of which are incorporated herein by reference in its entirety.

FIELD OF THE DISCLOSURE

The present disclosure relates generally to exemplary systems, methods and computer-accessible mediums for evaluating the safety risk associated with radio frequency emitting devices.

BACKGROUND INFORMATION

There has been a rapid development of wireless technology during the last decade. As of November 2011, there were more than 5.9 billion mobile phone users worldwide. (See e.g., Reference #1). As the number of users utilizing wireless devices increases, concerns have been raised with regard to the risk associated with the use of radio frequency ("RF") transmitting devices (e.g., mobile or cellular telephones). The concern can be even greater when considered along with the surge of the cancer incident rates over the past several decades. Mobile phones, and other RF transmitting devices, operate via a bidirectional transmission of radio waves at ultrahigh frequency (e.g., the radio to microwave range). Typical mobile phone communication systems operate between 800 MHz and 2700 MHz. At these frequencies, RF waves are supposedly non-ionizing (e.g., they do not carry enough energy to break chemical bonds). Nonetheless, being exposed to the RF radiation can result in increased heating of tissue via Joule and Dielectric heating mechanisms. Additionally, the ultimate effect of prolonged exposure to the use of an RF device is currently not known.

Specific Absorption Rate ("SAR") measures the rate at which energy from electro-magnetic ("EM") waves is absorbed by the body, and can be relevant in the safe usage of wireless devices, especially RF devices. (See e.g., Reference #2). SAR can depend on several factors, which can include the antenna and its position, the body's morphologic factor, the distance between the transmitting device and the head which can vary between individuals, and the power output of the device. Recent investigations have reported an increased incidence of malignant tumors in the head, brain, ear canal and parotid gland in connection with mobile phone usage. However, the difficulty associated with interpretation of the data from epidemiological studies has been described (see e.g., Reference #3), and the risk of cancer could not be confirmed. (See e.g., Reference #4). Studies have also shown an increase in evidence that RF EM fields (e.g., RF EM fields emitted by mobile phones) can potentially alter brain physiology (see e.g., References #5-11), and that a local exposure of tissue in the periphery and interior of the brain of young children is on average higher in comparison to adults. Assuming that there is no age dependence on the dielectric properties of the tissues, the reason is considered to be the closer vicinity of the RF currents to the brain of the child compared to the adult due to the age-dependent changes in proportions of the facial and skull regions. Additionally, the increased usage of mobile phones in children, as compared to adults, can also be a factor. While these results show that the RF radiation can alter the brain physiology, other studies suggest that a more detailed, qualified, analysis of the exposure and heating of the brain and its sub-regions is needed. (See e.g., Reference #12).

To quantify safety of wireless communication devices, cell phone makers and researchers model the wireless device using a numerical simulation such as the Finite-Difference-Time-Domain ("FDTD") method to visualize and quantify the resulting EM and SAR distributions inside a human body model. This simulation can be conducted with different orientations of the wireless device relative to an "average" human model. This simulation, however, can be innately flawed as it can be difficult to confirm that the actual induced fields inside the subject are the same as the simulated fields. While these simulations can provide some information regarding the local SAR distribution in the "average" human brain, it is not clear if they provide a realistic picture with regard to the actual exposure that individuals experience when using RF-transmitting devices, and more importantly, whether the device is safe for use. In addition to the utilization of simulation software to evaluate the local SAR generated by wireless communication devices, vendors also use homogeneous gel phantoms with temperature probes implanted in them. The wireless transmitting device can be activated next to the gel phantom, and the temperature change due to Joule and Dielectric heating mechanisms can be recorded. Even though the temperature is correlated with tissue damage, the use of a simple setup with a homogeneous gel phantom to mimic the complex anatomy of the human brain is too simplistic, and the conclusions that can be drawn with regard to the safe use of a specific device based on this type of testing can be misleading.

Generally, for a brief application of RF energy, the exposure duration may not be long enough for significant conductive or convective heat transfer to contribute to tissue temperature rise. In such case, the time rate of the rise in temperature is proportional to SAR. For longer exposure durations (e.g., when using mobile phones), RF energy-induced temperature rise can depend on the animal or tissue target, and their thermal regulatory behavior and active compensation process. For local or partial body exposures, if the amount of the RF energy absorbed is excessive, temperature rise and local tissue damage can occur. Under moderate conditions, a temperature rise on the order of 1° C. in humans and laboratory animals can result from an SAR input of 4 W/kg. However, this temperature rise falls within the normal range of human thermoregulatory capacity, and the heat increase alone cannot explain tissue damage. Nonetheless, under certain ambient environmental conditions where the temperature and humidity are already elevated, or where the heat capacity of the tissue is elevated and perfusion is low, the same SAR could produce body temperatures that reach well beyond normal levels permitted by the 1° C. increment, which can precipitate undesired heat-stress-related responses. The central premise of the exposure guidelines to protect exposed subjects against temperature increases could be eclipsed, breaching the temperature threshold for induction of adverse thermal effects. While the mechanism(s) of tissue heating which result from RF exposure are complex, it is possible that due to their complexity, and the limitations of our scientific knowledge, some mechanism(s) responsible for producing a significant effect(s) are still unknown. (See e.g., Reference #2).

Thus, it may be beneficial to provide exemplary systems, methods and computer-accessible mediums which are non-simulation based, which can quantify and assess the SAR-related risk with regard to RF transmitting device usage, and which can overcome at least some of the deficiencies described herein above.

SUMMARY OF EXEMPLARY EMBODIMENTS

Exemplary embodiments of the present disclosure relate to apparatus, systems and methods which are based on magnetic resonance imaging for safety evaluation of radio frequency emitting devices.

These and other objects of the present disclosure can be achieved through exemplary embodiments of exemplary systems, methods and computer-accessible mediums which can evaluate at least one radio frequency transmitting arrangement. Such exemplary evaluation can be performed, e.g., by receiving a first information associated with at least one scan of at least one live subject corresponding to effects of at least one radio frequency transmitting arrangement on the at least one live subject, and determining a second information based on the first information.

According to some exemplary embodiments of the present disclosure, the second information corresponds to an internal temperature of the live subject(s) and/or non-thermal reactions within the subject(s). The second information can be determined using referenceless magnetic resonance thermometry, which can use Proton's resonance frequency shift. The first information can be generated using a magnetic resonance imaging arrangement, a functional magnetic resonance imaging arrangement, a perfusion magnetic resonance imaging arrangement and/or a diffusion magnetic resonance imaging arrangement. The magnetic resonance imaging arrangement can be a full body scanner, a partial scanner and/or an open scanner.

In further exemplary embodiments of the present disclosure, the radio frequency transmitting arrangement can be a mobile phone. The radio frequency transmitting arrangement can also include at least one antenna placed within a scanning arrangement connected to at least one power arrangement placed far enough from the scanning arrangement so as to not to interfere with the scanning arrangement. The antenna(s) can be connected to the power arrangement(s) using a low-loss cable. The power arrangement(s) can be an external power amplifier. The live subject(s) can be an animal subject.

According to additional exemplary embodiments of the present disclosure, third information can be received which is associated with at least one scan of the live subject(s) corresponding to an absence of the effects of the radio frequency transmitting arrangement(s), and the second information can be determined based on the first information and the third information.

These and other objects, features and advantages of the present disclosure will become apparent upon reading the following detailed description of embodiments of the present disclosure, when taken in conjunction with the appended claims.

BRIEF DESCRIPTIONS OF THE DRAWINGS

Further objects, features and advantages of the present disclosure will become apparent from the following detailed description taken in conjunction with the accompanying Figures showing illustrative embodiments of the present disclosure, in which.

Figure 3:
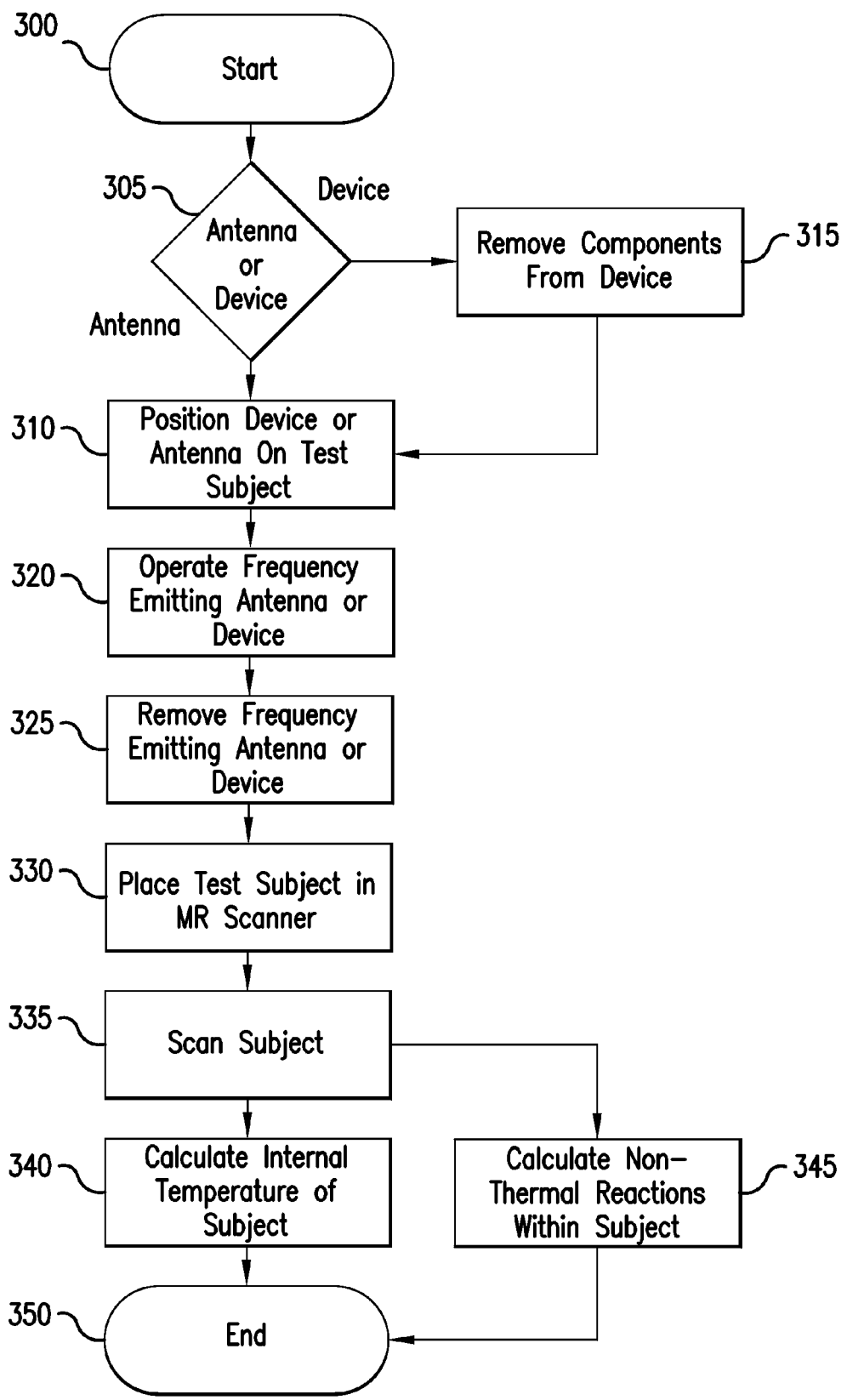
Figure 4:
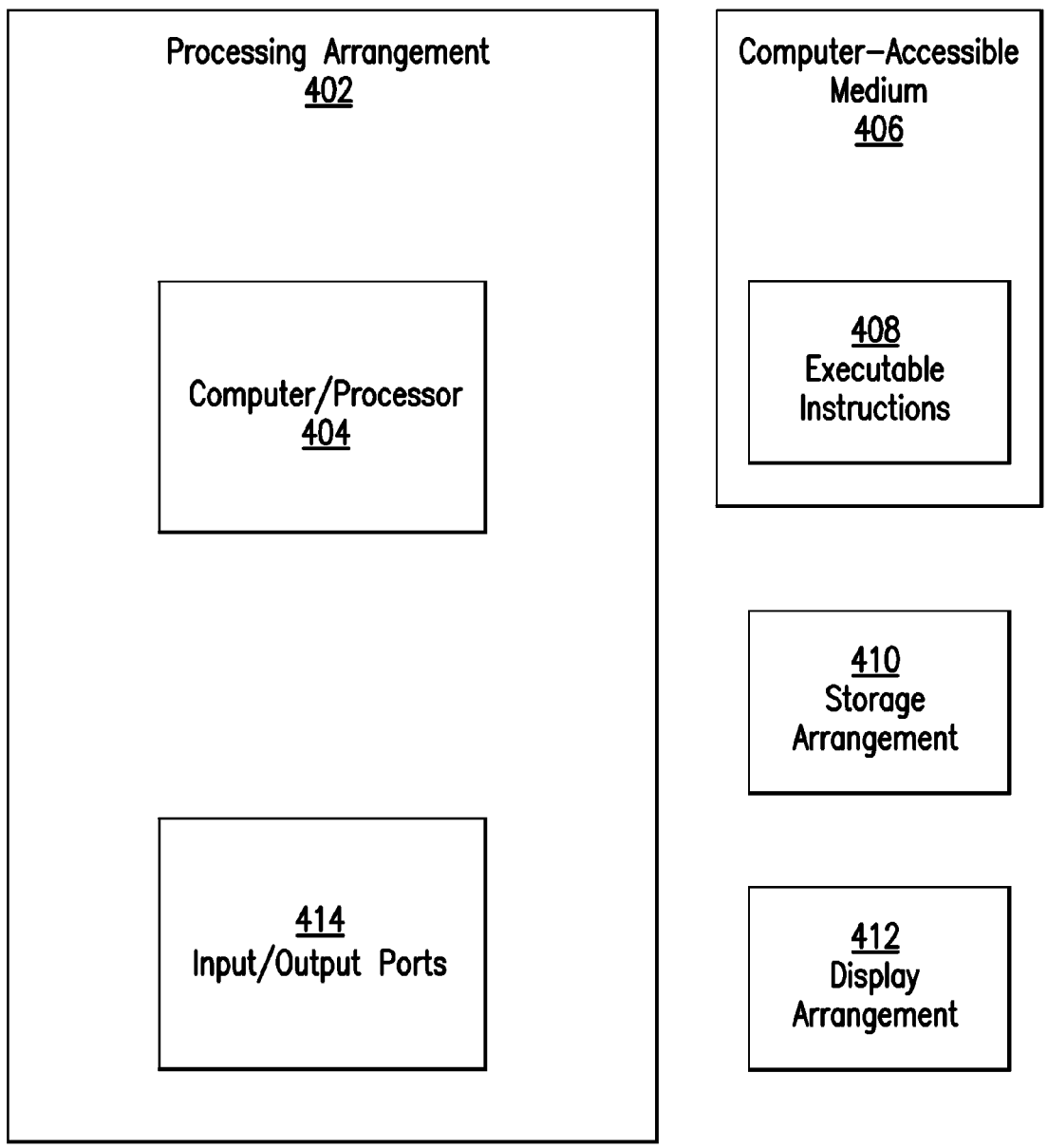

FIG. 3 is an exemplary flow diagram for a process to measure the risk associated with the RF emitting device according to another embodiment of the present disclosure; and FIG. 4 is an illustration of an exemplary block diagram of an exemplary system in accordance with certain exemplary embodiments of the present disclosure Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the subject disclosure as defined by the appended claims.

DETAILED DESCRIPTION OF EXEMPLARY EMBODIMENTS

Exemplary embodiments of the present disclosure relate to exemplary systems, methods and computer-accessible mediums for measuring the affects of RF fields using Magnetic Resonance Imaging ("MRI") scanners. In MRI, the operational frequency of the RF field can be centered on the larmor frequency (e.g., for a typical 3T scanner the operating frequency can be approximately 128 MHz). If the operating frequency of an RF wave is far from the larmor frequency (e.g., greater than approximately 100 KHz away) the wave may not interact with the spins in the body, and imaging of the body can be left unaltered. For example, a passive cell phone antenna operating at 800MHz could have essentially no effect on the image quality produced by a 3T MRI machine. However, even though the antenna operating at 800MHz can have no effect on the image quality produced by the MR machine, the RF field generated by the exemplary device can deposit power into the tissues, thus changing the local temperature of the subject. Since the carrier frequency of many RF transmitting devices can be far enough from the larmor frequency of the scanner, and the bandwidth of the transmitting devices can be relatively narrow, the exemplary systems, methods and computer-accessible mediums of the present disclosure can position the transmitting antenna inside the scanner room while being configured to attain the same anatomical or functional information from the scanner.

The MRI magnet can be located inside a shielded room. The distance of the machine from the shield can vary based on the strength of the magnet, the structure of the magnet, as well as other factors. This shield can typically be used to remove interference from RF waves that can enter into the scanner room from outside of the scanner room. For example, a typical 3T machine operates at a frequency of 128 MHz, which can be in the frequency range of frequency modulation ("FM") such as very high frequency ("VHF"). These waves can easily cause artifacts in the images if the room is not shielded.

In the case of cell phone technology, the exemplary systems, methods and computer-accessible mediums can be based on adaptations of the code division multiple access ("CDMA") and/or time division multiple access ("TDMA") networks. Radio waves emitted by a global system for mobile ("GSM") handset can have peak power of up to 2 Watts, and a U.S. analogue phone can have a maximum transmit power of 3.6 Watts, where the maximum power output can generally be regulated by a mobile phone standard, and by the regulatory agencies in each country. (See e.g., Reference #1). In exemplary mobile phone systems, an "adaptive power control" scheme can be utilized where the power that is likely generated by the phone can vary during a conversation according to the amount of interference with the signal. An increase in output power can be seen when the user is situated far away from a mobile phone transmission base-station or in areas with poor reception due to an electric shielding (e.g., in elevators). For other wireless modalities, similar "adaptive power control" can be utilized, however, the maximum output power can be different.

According to certain exemplary embodiments of the present disclosure, exemplary systems, methods and computer-accessible mediums can be provided which can facilitate the utilization of MRI techniques for the analysis of the risk associate with RF transmitting devices. While generally no electrical devices are allowed to be in an MR scanner room because the magnetic field can alter the operation of the electronic device positioned inside the bore off the magnet, the exemplary systems, methods and computer-accessible mediums can overcome this requirement by defining a few frameworks which can depend on the specific transmitting device that can facilitate the RF transmitting devices to operate inside the scanner room.

Figure 1A:
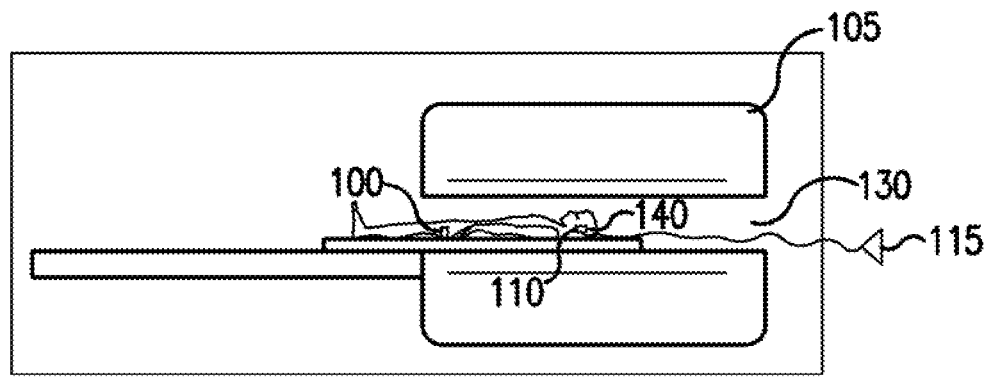
FIG. 1A is an illustration of a system for determining the risk associated with an RF emitting device using an exemplary antenna connected to an exemplary external power amplifier according to an exemplary embodiment of the present disclosure.

FIG. 1A illustrates a system for determining the risk associated with an RF emitting device using an exemplary antenna connected to an exemplary external power amplifier according to an exemplary embodiment of the present disclosure. The exemplary system includes an exemplary transmitting device 110 that can be attached or placed near a subject 100. The exemplary transmitting device 110 can be modified to remove therefrom its active and magnetic components (e.g., CPU, battery, etc.). An exemplary external power amplifier 115, which can be inside or outside of the room that the test is being performed in, can then be connected to the antenna of the exemplary transmitting device driving the same or a similar amount of power as normally utilized by the device. The subject 100 and the exemplary transmitting device 110 can be placed inside of an MR scanner/machine 105. An analysis of the risk associated with the RF transmitting device can then be measured inside the bore 130 of the scanner in real time.

Figure 1B:
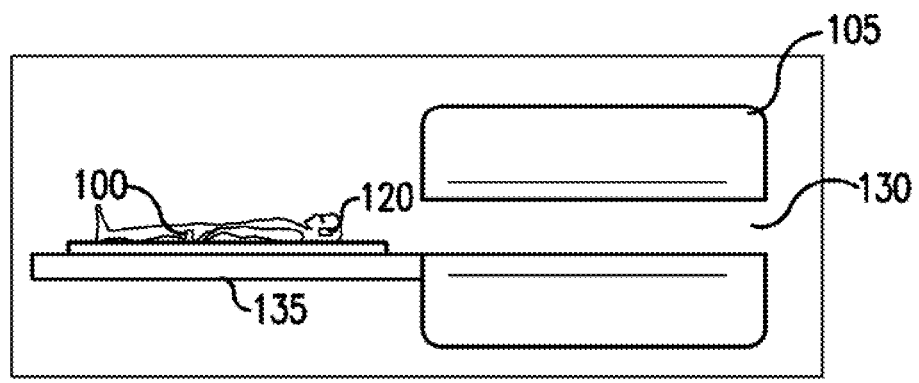
FIG. 1B is an illustration of a system for determining the risk associated with the RF emitting device with the transmitting device inside the scanner room, outside a bore of the scanner, according to the exemplary embodiment of the present disclosure.

As shown in FIG. 1B, an exemplary transmitting device 120 can be provided which can be left intact (e.g., none of the magnetic components being removed), and turned on inside the scanner room on the scanner table 135, although being located outside a bore 130 of the MR scanner/machine 105. Imaging of at least one portion of the subject 100 can then be conducted before and after the exemplary transmitting device 120 is operated.

Figure 1C:
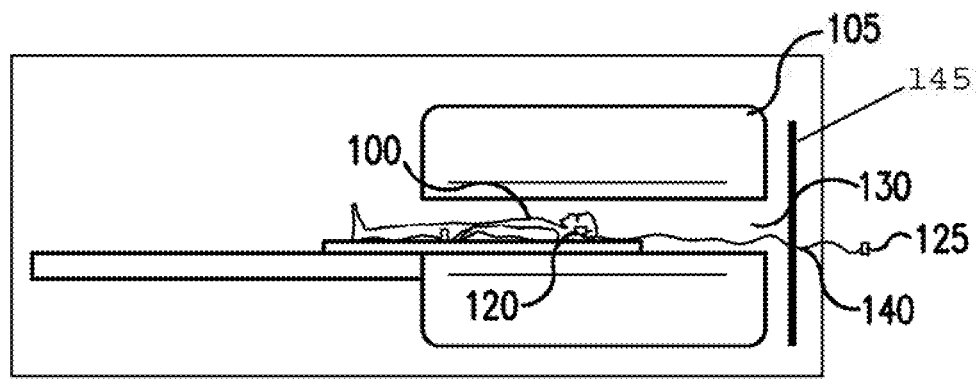
FIG. 1C is a system for determining the risk associated with the RF emitting device using the exemplary antenna connected to an exemplary low-loss cable according another exemplary embodiment of the present disclosure.

As shown in FIG. 1C, an exemplary transmitting device 125 can be provided which can have its components extracted, except for the transmitting antenna 120, and can be located outside the scanner area of MR scanner 105. The antenna 120 can be connected via a low-loss cable 140, or other suitable cable, to the remaining components (e.g., the previously extracted components) of the exemplary transmitting device 125, such as a mobile phone, which can be placed inside or outside of the scanner room, depending on the device and how the device is driven.

An exemplary apparatus 140 (as shown in the system of FIG. 1A) can be provided that holds the transmitting device substantially steady or approximately immobile within the scanner during scanning (e.g., to facilitate the safe operation of the device and a consistent position of the device relative to the subject). The exemplary systems, methods and computer-accessible mediums can be used to image the brain, different tissues, and areas of the body other than the brain. The exemplary systems, methods and computer-accessible mediums can then be used to evaluate both thermal and non-thermal effects on the human body.

Exemplary Evaluation of the Thermal Effect

Penne's' bio-heat equation describes the thermal energy balance for perfused tissue as:

$$\rho C \frac{\partial T}{\partial t} = \nabla \cdot (k \nabla T) + h_b + h_e \qquad (1)$$

Where $\rho$, $C$ and $k$ refer to tissue density, specific heat capacity and thermal conductivity $$\left( \frac{\text{Watts}}{m - K} \right),$$

r and $h_b$ can be the blood-to-tissue heat transfer rate. The RF energy deposition rate can be expressed by $h_e$ $$\left( \frac{\text{Watts}}{m^3} \right),$$

which can be a driving force for temperature rise as result of Joule and Dielectric heating mechanisms. Since temperature change can be correlated with tissue damage, (see e.g., References #13; 14) the exemplary systems, methods and computer-accessible mediums can track in-vivo temperature change. Generally, MR temperature mapping can use the Proton Resonance Frequency shift ("PRF"). (See e.g., References #12; 16; 17). The nuclear field experienced by the spins can be expressed as:

$$B_{nuc} = \left( 1 - \sigma(T) - \frac{2\chi}{3} \right) B_0 \qquad (2)$$

In equation 2, $\sigma(T)$ can express the temperature dependent chemical shift, x can express the bulk magnetic susceptibility and $B_0$ can express the static magnetic field strength. The temperature dependent chemical shift (in parts per million) can be defined as:

$$\sigma(T) = \sigma_0 + \sigma_T(T) \quad (3)$$

Where $\sigma_0$ can represent the static magnetic field in homogeneities and $\sigma_T(T)$ can express the temperature dependent contribution for the chemical shift. The chemical shift can be calculated from the phase information in spoiled gradient echo images (see e.g., Reference #18) as:

$$\phi(T) = \gamma \sigma(T) TE B_0 \quad (4)$$

Where $\Phi(T)$ can express the temperature dependent phase map, $\gamma$ can express the gyromagnetic ratio of protons (42.58*106 Hz/T) and TE can express the echo time of the gradient echo sequence. In order to measure temperature dependent chemical changes, $\sigma_0$ can be accounted for. This can be accomplished by obtaining a reference image before RF heating, and subtracting the reference image from the phase image after heating; the temperature change can be expressed as:

$$\Delta T = T - T_{ref} = \frac{\phi(T) - \phi(T_{ref})}{\alpha \gamma TE B_0} \quad (5)$$

Where $\alpha$ can express the temperature dependency of the chemical shift (in PPM/C~0.01 PPM/C).

The exemplary systems, methods and computer-accessible mediums can utilize a referenceless MR thermometry for in vivo measurement of temperature change due to RF power deposition (e.g., using known in-vivo applications). (See e.g., Reference #19). A plurality of RF antennas can be used (e.g., by operating at a different frequencies than the MR scanner), and all of the plurality of RF antennas can be used inside the scanner room, which is advantageous compared to current schemes that attempt to quantify the safe use of RF transmitting devices using hypothetical simulation results on "average" subjects or finite temperature measurements on homogeneous gel phantoms.

Exemplary Absolute Temperature Mapping Using Exogenous Molecules

MR thermometry using the Proton's (e.g., hydrogen-1) resonance frequency shift can provide high temporal and spatial resolution, and can have limited temperature sensitivity (e.g., 0.01 ppm/C). The exemplary systems, methods and computer-accessible mediums can utilize paramagnetic compounds can also utilize other nuclei which can include helium-3, lithium-7, carbon-13, fluorine-19, oxygen-17, sodium-23, phosphorus-31 and xenon-129, although not limited thereto. The exemplary systems, methods and computer-accessible mediums can also utilize paramagnetic compounds (e.g., temperature sensitive Thulium 1,4,7,10-Tetraazacyclododecane-1,4,7,10-Tetramethyl-1,4,7,10-Tetraacetic Acid (TmDOTMA)), which can be approximately 60 times more sensitive to temperature change. (See e.g., Reference #20). The compound can provide temperature imaging that can be insensitive to inhomogeneity of the main magnetic field. Additionally, utilization of such compounds in phantoms can facilitate an absolute temperature accuracy of less than 0.1 degrees centigrade.

Exemplary Non-Thermal Effect Evaluation

The exemplary systems, methods and computer-accessible mediums can also facilitate the measuring of non-thermal effects. For example, researchers have reported physiological changes in the brain after a subject's usage of cell phones. (See e.g., References #21-23) In such studies, Positron Emission Tomography ("PET") imaging was used to look at glucose consumption in the brain. The exemplary systems, methods and computer-accessible mediums can utilize functional MRI ("fMRI"), and/or perfusion and diffusion MRI, to evaluate changes in the body that can be correlated to RF transmission, as well as to understand the physiological changes in the body due to RF power deposition.

The ability to monitor the safety of RF transmitting devices, such as mobile phones, can be improved utilizing the exemplary systems, methods and computer-accessible mediums. Traditionally, EM field numerical simulations have been used to describe interactions of EM fields with the body, and provide temporal and spatial information about the internal variation of electric fields, magnetic fields, currents and energy deposition. Although these numerical simulations can be useful, they can lack precision. Among the significant weaknesses of these simulations can be the preciseness and accuracy of the simulation-designed models in comparison with "real life" conditions. In addition, the anatomy of the "real life" subject can differ from the anatomy of the body mesh used for simulation, and certain assumptions need to be made regarding the boundary conditions that may or may not be true. This discrepancy between EM numerical simulations and the true distributions of electric fields, magnetic fields, currents and, most importantly, energy deposition, can be a major concern for relying on simulations to ensure safe operation of RF transmitting devices. Rather than relying on hypothetical simulation models, and hypothetical discretized bodies, the exemplary systems, methods and computer-accessible mediums can provide a beneficial way of measuring subject specific RF power deposition, in-vivo, for a multitude of RF transmitting devices. The exemplary systems, methods and computer-accessible mediums can measure the change in temperature in response to RF heating, and because temperature change can be correlated with tissue damage, the exemplary systems, methods and computer-accessible mediums offers a novel, and more accurate, way to estimate the risk associated with the usage of RF transmitting devices. The exemplary systems, methods and computer-accessible mediums can be applied in a subject-specific manner, and can be used for any number of RF transmitting devices and orientations relative to the body.

The exemplary systems, methods and computer-accessible mediums can utilize any suitable MR scanning technology (e.g., full body scanners, partial and/or "open" scanners, large animal scanners, custom designed scanners, or any other MR scanning arrangement). The test material can include any living organism, including animals, mammals, humans, or any suitable artificial material, including materials meant to simulate a living organism.

Various apparatus, systems and/or methods according to the exemplary embodiments of the present disclosure can be used for an evaluation of the exposure of the human brain and phantoms (e.g., artificial materials used to simulate human subjects)to RF mobile phone radiation. Additional exemplary applications can include an evaluation of Wi-Fi, cell phone, Bluetooth, cordless phones, two-way radios, walkie talkies, microwaves, radio waves and any other antenna using MR, as long as the wavelength of the transmitting antenna is different than the operating frequency of the MR machine. Any frequency emitting device and/or electromagnetic emitting device can be used in conjunction with the exemplary systems, methods and computer-accessible mediums. Additionally, the exemplary systems, methods and computer-accessible mediums can include a barrier 145 to contain or block radiation (e.g., MR radiation), and can include a shield or shielding, which can be the same as or separate from the barrier 145.

Figure 2:
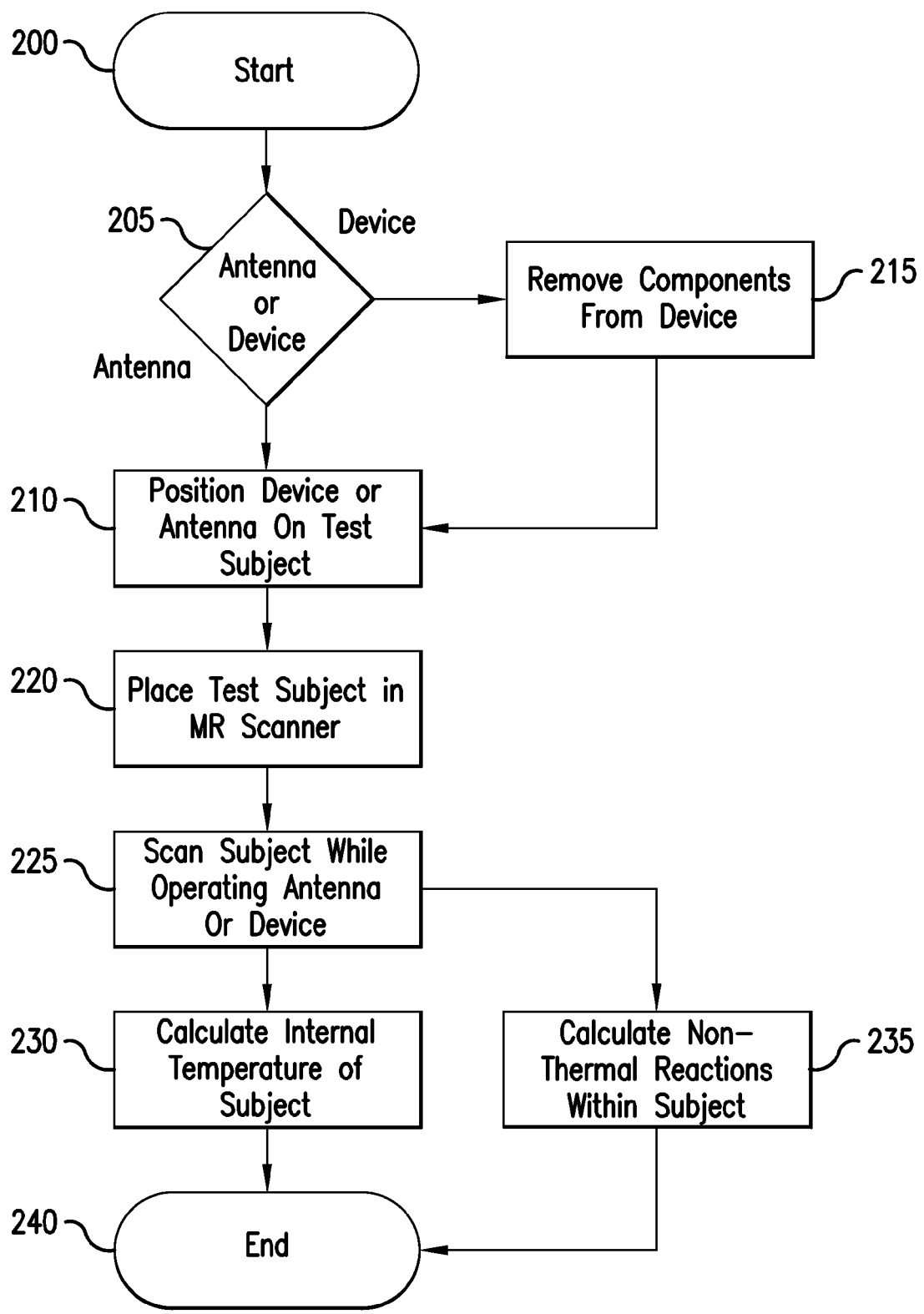
FIG. 2 is an exemplary flow diagram for measuring a risk associated with the RF emitting device according to an exemplary embodiment of the present disclosure.

FIG. 2 shows an exemplary flow diagram of a process/method for assessing the risk of exposure to an RF emitting device according to an exemplary embodiment of the present disclosure. The exemplary process/method begins at block 200. For example, at procedure 205, a determination can be made as to whether to utilize only an antenna, being driven with components that can be located outside of the scanner area, or whether to utilize a device. If only the antenna is used, then the antenna can be positioned on the test subject at procedure 210. If the device is used, the battery, CPU and/or other electronic and/or metal components can be removed, or confirmed as previously removed, at procedure 215. Then, at procedure 210, the device can be positioned on the test subject. At procedure 220, the test subject and the antenna or device can be placed in the MR scanner, and the exemplary systems, methods and computer-accessible mediums can be used to scan the subject while operating the frequency emitting antenna or device at procedure 225. At procedure 230, the exemplary systems, methods and computer-accessible mediums can determine and/or calculate an internal temperature of the subject from scan data, and/or calculate non-thermal reactions within the subject from the scan data at procedure 235. At block 240, the exemplary method can end, and the data can be stored for later use.

FIG. 3 shows an exemplary flow diagram of the process/method for assessing the risk of exposure to an RF emitting device according to another exemplary embodiment of the present disclosure. The exemplary process/method of FIG. 3 begins at block 300. At procedure 305, a determination can be made as to whether to utilize only the antenna, being driven with components that can be located outside of the scanner area, or whether to utilize the device. If only the antenna is used, then the antenna can be positioned on the test subject at procedure 310. If the device is used, the battery, CPU and/or other electronic and/or metal components can be removed, or confirmed as previously removed, at procedure 315. Then, at procedure 310, the device can be positioned on the test subject. At procedure 320, the frequency emitting antenna can be operated for some period of time. After, the frequency emitting antenna and/or device has been operated, it can be removed at procedure 325, and the test subject can be placed in the MR scanner at procedure 330, and the exemplary systems, methods and computer-accessible mediums can scan the subject at procedure 335. At procedure 340, the exemplary systems, methods and computer-accessible mediums can calculate an internal temperature of the subject from scan data, and/or calculate non-thermal reactions within the subject from the scan data at procedure 345. At block 350, the exemplary process/method can end, and the data can be stored for later use. Additionally, the test subject can be scanned prior to procedure 310, and a before and after comparison of the scans can be used for detecting thermal or non-thermal reactions within the test subject.

FIG. 4 shows a block diagram of an exemplary embodiment of a system according to the present disclosure which can be used to calculate and assess the risk of exposure from an RF emitting device. For example, exemplary procedures in accordance with the present disclosure described herein can be performed by a processing arrangement and/or a computing arrangement 402. Such processing/computing arrangement 402 can be, e.g., entirely or a part of, or include, but not limited to, a computer/processor 404 that can include, e.g., one or more microprocessors, and use instructions stored on a computer-accessible medium (e.g., RAM, ROM, hard drive, or other storage device).

As shown in FIG. 4, e.g., a computer-accessible medium 406 (e.g., as described herein above, a storage device such as a hard disk, floppy disk, memory stick, CD-ROM, RAM, ROM, etc., or a collection thereof) can be provided (e.g., in communication with the processing arrangement 402). The computer-accessible medium 406 can contain executable instructions 408 thereon. In addition or alternatively, a storage arrangement 410 can be provided separately from the computer-accessible medium 406, which can provide the instructions to the processing arrangement 402 so as to configure the processing arrangement to execute certain exemplary procedures, processes and methods, as described herein above, for example.

Further, the exemplary processing arrangement 402 can be provided with or include an input/output arrangement 414, which can include, e.g., a wired network, a wireless network, the interne, an intranet, a data collection probe, a sensor, etc. As shown in FIG. 4, the exemplary processing arrangement 402 can be in communication with an exemplary display arrangement 412, which, according to certain exemplary embodiments of the present disclosure, can be a touch-screen configured for inputting information to the processing arrangement in addition to outputting information from the processing arrangement, for example. Further, the exemplary display 412 and/or a storage arrangement 410 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, e.g., data and information.

It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly incorporated herein in its entirety.

It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

[1] Wikipedia. Mobile Phone, http://en.wikipedia.org/wiki/Mobile_phone_radiation_and_health.

[2] ICNIRP, "Exposure to high frequency electromagnetic fields, biological effects and health consequences" (100 kHz-300 GHz). (2009).

[3] Cardis, "Brain tumour risk in relation to mobile telephone use: results of the INTERPHONE international case-control study," Int. J. Epidemiol, Volume 39, pg. 675 (2010).

[4] Khurana, V.G. et al., "Cell phones and brain tumors: a review including the long-term epidemiologic data," Surg. Neurol, Volume 72, pg. 205 (2009).

[5] Borbely, A. A. et al., "Pulsed high-frequency electromagnetic field affects human sleep and sleep electroencephalogram," Neurosci. Lett., Volume 275, pg. 207 (1999).

[6] Croft, R. J. et al., "The effect of mobile phone electromagnetic fields on the alpha rhythm of human electroencephalogram," Bioelectromagnetics, Volume 29, pg. 1 (2008).

[7] Huber, R. et al., "Radio frequency electromagnetic field exposure in humans: estimation of SAR distribution in the brain, effects on sleep and heart rate," Bioelectromagnetics, Volume 24, pg. 262 (2003).

[8] Loughran, S. P. et al., "The effect of electromagnetic fields emitted by mobile phones on human sleep," Neuroreport, Volume 16, pg. 1973 (2005).

[9] Luria, R. et al., "Cognitive effects of radiation emitted by cellular phones: the influence of exposure side and time," Bioelectromagnetics, Volume 30, pg. 198 (2009).

[10] Regel, S. J. et al., "Pulsed radio frequency radiation affects cognitive performance and the waking electroencephalogram," Neuroreport, Volume 18, pg. 803 (2007).

[11] Regel, S. J. et aL, "Pulsed radio-frequency electromagnetic fields: dose-dependent effects on sleep, the sleep EEG and cognitive performance," J. Sleep Res., Volume 16, pg. 253 (2007).

[12] Crespo-Valero, P. et al., "Novel methodology to characterize electromagnetic exposure of the brain," Physics in Medicine and Biology, Volume 56, pgs. 383-396 (2011).

[13] Bicher, H. I., "The physiological effects of hyperthermia," Radiology, Volume 137, pgs. 511-513 (1980).

[14] Bicher, H. I. et al., "Local hyperthermia for deep tumors," Adv Exp Med Biol., Volume 267, pgs. 411-422 (1990).

[15] Ishihara, Y. et al., "A precise and fast temperature mapping using water proton chemical shift," Magn Reson Med, Volume 34, pgs. 814-823 (1995).

[16] De Poorter, J., "Noninvasive MRI thermometry with the proton resonance frequency method: study of susceptibility effects," Magn Reson Med, Volume 34, pgs. 359-367 (1995).

[17] De Poorter, J. et al., "Noninvasive MRI thermometry with the proton resonance frequency (PRF) method: in vivo results in human muscle," Magn Reson Med, Volume 33, pgs. 74-81 (1995).

[18] Denis de Senneville, B. et al., "Magnetic resonance temperature imaging," Int J Hyperthermia, Volume 21, pgs. 515-531 (2005).

[19] Rieke, V. et al., "Referenceless MR thermometry for monitoring thermal ablation in the prostate," IEEE Trans Med Imaging, Volume 26, pgs. 813-821 (2007).

[20] Hekmatyar, S. K. et al., "Noninvasive MR thermometry using paramagnetic lanthanide complexes of 1,4,7,10-tetraazacyclodoecane-alpha,alpha',alpha'',alpha'''-tetramethyl-1,4,7,10-tetraacetic acid (DOTMA4-)," Magnetic resonance in medicine : official journal of the Society of Magnetic Resonance in Medicine/Society of Magnetic Resonance in Medicine, Volume 53, pgs. 294-303 (2005).

[21] Kosowsky, A., et al., "Cell phone activation and brain glucose metabolism," JAMA, Volume 305, pgs. 2066; 2067-2068 (2011).

[22] Lai, H et al., "Cell phone radiofrequency radiation exposure and brain glucose metabolism," JAMA: the journal of the American Medical Association, Volume 305, pgs. 828-829 (2011).

[23] Volkow, N. D. et al., "Effects of cell phone radiofrequency signal exposure on brain glucose metabolism," JAMA Volume 305, pgs. 808-813, (2011).

[24] "Is there a link between cell phone use and cancer?," Mayo Clinic Womens Healthsource Volume 15, pg. 8. (2011).

[25] A, C., "The Virtual Family-development of surface-based anatomical models of two adults and two children for dosimetric simulation," Phys. Med. Biol. Volume 55, pg. N23 (2010).

[26] Ahlbohm, A. et al., "Epidemiologic evidence on mobile phones and tumor risk: a review," Epidemiology Volume 20, pg. 639 (2009).

[27] Anderson, V. et al., "Measurements of skin surface temperature during mobile phone use," Bioelectromagnetics Volume 28, pgs. 159-162, (2007).

[28] Beard, B. et al., "Comparisons of computed mobile phone induced SAR in the SAM phantom to that in anatomically correct models of the human head," IEEE Trans. Electromagn. Volume 48, pg. 397 (2006).

[29] Beard, B. B. et al., "Comparisons of computed mobile phone induced SAR in the SAM phantom to that in anatomically correct models of the human head," Electromagnetic Compatibility, IEEE Transactions Volume 48, pgs. 397-407 (2006).

[30] Blackman, C., "Cell phone radiation: Evidence from ELF and RF studies supporting more inclusive risk identification and assessment," Pathophysiology Volume 16, pgs. 205-216, (2009).

[31] Boniol, M. et al., "(2011) Association between number of cell phone contracts and brain tumor incidence in nineteen U.S. States," J Neurooncol Volume 101, pgs. 505-507. J. Neurooncol (2011).

[32] Cardis, E. et al., "Risk of brain tumours in relation to estimated RF dose from mobile phones: results from five Interphone countries," Occup Environ Med, 2011.

[33] Cardis, E. et al., "Distribution of RF energy emitted by mobile phones in anatomical structures of the brain," Phys Med Bio Volume 153, pgs. 2771-2783, (2008).

[34] Cardis, E. et al., "Estimation of RF energy absorbed in the brain from mobile phones in the Interphone Study," Occup Environ Med, 2011 (2011).

[35] Cardis E., et al., "Distribution of RF energy emitted by mobile phones in anatomical structures of the brain," Phys. Med. Biol.Volume 53, pg.-2771 (2008).

[36] Chavdoula, E. D. et al., "Comparison of biological effects between continuous and intermittent exposure to GSM-900-MHz mobile phone radiation: Detection of apoptotic cell-death features," Mutat Res Volume 700, pgs. 51-61, (2010).

[37] Christ, A. et al., "Age dependent tissue-specific exposure of cell phone users," Phys. Med. Biol Volume 55, pg. 1767 (2010).

[38] Christopoulou M. et al., "Electromagnetic exposure of the brain functional regions in adults and children," Internal Report (2010).

[39] Deltour, I. et al., "Analysis of three-dimensional SAR distributions emitted by mobile phones in an epidemiological perspective," Bioelectromagnetics, (2011).

[40] Dendy, P. P., "Mobile phones and the illusory pursuit of safety," Lancet Volume 356, pgs. 1782-1783, (2000).

[41] French, P. W. et al., "Mobile phones, heat shock proteins and cancer," Differentiation Volume 67, pgs.-93-97, (2001).

[42] Gabriel, S. et al., "The dielectric properties of biological tissues: III. Parametric models for the dielectric spectrum of tissues," Phys. Med. Biol. Volume 41, pg. 2271 (1996).,

[43] Gosselin, M-C et al., "Estimation of head-tissue specific exposure from mobile phones, based on measurements in the homogeneous SAM head," Bioelectromagnetics (2010).

[44] Gutschi, T. et al., "Impact of cell phone use on men's semen parameters," Andrologia, Volume 10., pgs. 1111-1439 (2011).

[45] Hamblin, D. L. et al., "EEG electrode caps can reduce SAR induced in the head by GSM900 mobile phones," IEEE Trans Biomed Eng Volume 54, pgs. 914-920 (2007).

[46] Han, Y. Y. et al., "Cell phone use and acoustic neuroma: the need for standardized questionnaires and access to industry data," Surg NeuroVolume 172, pgs. 216-222; (2009).

[47] Hu, Q, Q. G., "Fast, accurate, and automatic extraction of the modified talairach cortical landmarks from magnetic resonance images," Magn. Reson. Med. Volume 53, pg. 970 (2005).

[48] IEEE, "Technical Report" (2008).

[49] Kainz, W et al., "Dosimetric comparison of the specific anthropomorphic mannequin (SAM) to 14 anatomical head models using a novel definition for the mobile phone positioning," Phys. Med. Biol Volume.50, pg. 3423 (2005).

[50] Kheifets, L et al., "The sensitivity of children to electromagnetic fields," Pediatrics Volume 116, pg. 303 (2005).

[51] Khurana, V. G. et al., "Health risks of cell phone technology," Surg Neuro Volume 172, pgs. 436-437; (2009).

[52] Khurana, V.G. et al., "Health risks of cell phone technology," Surgical neurology Volume 72, pgs. 436-437 (2009).

[53] Kim, D. W. et al., "Physiological effects of RF exposure on hypersensitive people by a cell phone," Conf Proc IEEE Eng Med Biol Soc pgs. 2322-2325, (2008).

[54] Kivekas, O. et al., "Bandwidth, SAR, and efficiency of internal mobile phone antennas," Electromagnetic Compatibility, IEEE Transactions on Volume 46, pgs. 71-86 (2004).

[55] Kumar, N. R. et al., "Exposure to cell phone radiations produces biochemical changes in worker honey bees," Toxicol Int Volume 18, pgs. 70-72, (2011).

[56] Kumar, N. R. et al., "Exposure to cell phone radiations produces biochemical changes in worker honey bees," Toxicology internationall Volume 8, pgs. 70-72, (2011).

[57] Lancaster, J L et al., "Automated labeling of the human brain: a preliminary report on the development and evaluation of a forward-transform method," Hum. Brain Mapp Volume .5, pg. 238, (1997).

[58] Lancaster, J L et al., "Automated Talairach atlas labels for functional brain mapping," Hum. Brain Mapp. Volume 10, pg.-120 (2000).

[59] Lehrer, S. et al., "Association between number of cell phone contracts and brain tumor incidence in nineteen U.S. States," Journal of neuro-oncology Volume 101, pgs. 505-507, (2011).

[60] Lonn, S. et al., "Output power levels from mobile phones in different geographical areas; implications for exposure assessment," Occup Environ Med Volume 61, pgs. 769-772, (2004).

[61] M, W. K. W. S. T., "Estimation of 3D SAR distributions from mobile phone compliance testing data for the local exposure assessment in epidemiological study," Proc. 28th URSI General Assembly (2005).

[62] Mailankot, M. et al., "Radio frequency electromagnetic radiation (RF-EMR) from GSM (0.9/1.8GHz) mobile phones induces oxidative stress and reduces sperm motility in rats," Clinics (Sao Paulo) Volume 64, pgs. 561-565, (2009).

[63] Marino, A. A. et al., "Nonlinear changes in brain electrical activity due to cell phone radiation," Bioelectromagnetics Volume 24, 339-346, (2003).

[64] McIntosh, R. L. et al., "Assessment of SAR and thermal changes near a cochlear implant system for mobile phone type exposures," Bioelectromagnetics Volume 29, pgs. 71-80, (2008).

[65] Minelli, T. A. et al., "Modeling cell dynamics under mobile phone radiation," Nonlinear Dynamics Psychol Life Sci Volume 11, pgs.197-218 (2007).

[66] "Effects of heterogeneous tissue distribution in a human head on the exposure to mobile phones: influence on epidemiologic studies," Proc. 32nd Annu. Meeting of the Bioelectromagnetics Society (2010).

[67] Nordstrom, C.H., "Cell phone activation and brain glucose metabolism," JAMA Volume 305, pg. 2067; (2011).

[68] Nowinski, "Modified Talairach landmarks," Acta Neurochir. Volume143, pg. 1045 (2001).

[69] Parkar, M. A. et al., "Effect of cell phone exposure on physiologic and hematologic parameters of male medical students of Bijapur (Karnataka) with reference to serum lipid profile," Journal of basic and clinical physiology and pharmacology Volume 21, pgs. 201-210 (2010).

[70] Peres, J., "WHO Classification Sparks Debate Over Cell Phone Safety," Journal of the National Cancer Institute Volume 103, pgs. 1146-1147, (2011).

[71] Rothman, K. J., "Epidemiological evidence on health risks of cellular telephones," Lancet Volume 356, pgs. 1837-1840, (2000).

[72] Singh, H. P. et al., "Cell phone electromagnetic field radiations affect rhizogenesis through impairment of biochemical processes," Environ Monit Assess, Volume 10, (2011).

[73] Straume, A. et al., "Skin temperature increase caused by a mobile phone: a methodological infrared camera study," Bioelectromagnetics Volume 26, pgs. 510-519, (2005).

[74] Taflove, A, H. S. C., "Computational Electromagnetics: The Finite-Difference Time-Domain Method," (2000).

[75] Talairach, J, T. P., "Co-Planar Stereotaxic Atlas of the Human Brain," (1988).

[76] Toga, A W, M. J. C., "Brain Mapping: The Systems," (2000).

[77] Ventura, G. J., "A cell phone and a Chinese curse. Med Humanit Volume 36, pg. 57," (2010).
[78] Vogel, G., "Scientific misconduct. Fraud charges cast doubt on claims of DNA damage from cell phone fields," Science Volume 321, pgs.1144-1145, (2008).
[79] Walsh, B., "Cell-phone safety," Time Volume 175, pgs. 47-49 (2010).
[80] Wiart J, H. A., et al., "Analysis of RF exposure in the head tissues of children and adults," Phys. Med. Biol. Volume 53, pg. 3681 (2008).
[81] Wiedemann, P. M., et al., "[SAR values of mobile phones. Safety evaluation and risk perception]. Bundesgesundheitsblatt Gesundheitsforschung Gesundheitsschutz Volume 49," pgs. 211-216, (2006).
[82] Yan, J. G., et al., "Upregulation of specific mRNA levels in rat brain after cell phone exposure," Electromagn Biol Med Volume 27, pgs. 147-154, (2008).
[83] Alon, L., "Local SAR Calibration and Prediction Model in Parallel Transmit," MRI. ISMRM (2010).

What is claimed is:

1. A non-transitory computer-accessible medium having stored thereon computer-executable instructions for evaluating at least one radio frequency (RF) transmitting arrangement, wherein, when a computer hardware arrangement executes the instructions, the computer arrangement is configured to perform procedures comprising:
   activating the at least one RF transmitting arrangement while a scanner table of a magnetic resonance (MR) scanning arrangement which has at least one live subject thereon is located outside of a scanner bore of the MR scanning arrangement;
   causing a movement of the scanner table which has the at least one live subject thereon inside of the bore;
   receiving a first information associated with at least one scan of the at least one live subject provided on the scanner table inside the bore corresponding to at least one effect of the at least one RF transmitting arrangement on the at least one live subject; and
   determining a second information based on the first information.

2. The non-transitory computer-accessible medium of claim 1, wherein the second information corresponds to an internal temperature of the at least one live subject.

3. The non-transitory computer-accessible medium of claim 1, wherein the second information corresponds to at least one non-thermal reactions within the at least one live subject.

4. The non-transitory computer-accessible medium of claim 1, wherein the second information is determined using a referenceless magnetic resonance thermometry.

5. The non-transitory computer-accessible medium of claim 4, wherein the referenceless magnetic resonance thermometry uses Proton's resonance frequency shift.

6. The non-transitory computer-accessible medium of claim 1, wherein the first information is generated using the MR scanning arrangement, and wherein the MR scanning arrangement includes at least one of a magnetic resonance imaging arrangement, a functional magnetic resonance imaging arrangement, a perfusion magnetic resonance imaging arrangement or a diffusion magnetic resonance imaging arrangement.

7. The non-transitory computer-accessible medium of claim 1, wherein the MR scanning arrangement is at least one of a full body scanner, a partial scanner or an open scanner.

8. The non-transitory computer-accessible medium of claim 1, wherein the at least one RF transmitting arrangement is a mobile phone.

9. The non-transitory computer-accessible medium of claim 1, wherein the at least one RF transmitting arrangement comprises at least one antenna placed on the scanner table connected to at least one power arrangement placed at a particular distance from the scanning arrangement so as to not interfere with the scanning arrangement.

10. The non-transitory computer-accessible medium of claim 9, wherein the at least one antenna is connected to the at least one power arrangement using a low-loss cable.

11. The non-transitory computer-accessible medium of claim 9, wherein the at least one power arrangement is an external power amplifier.

12. The non-transitory computer-accessible medium of claim 1, wherein the at least one live subject is an animal subject.

13. The non-transitory computer-accessible medium of claim 1, further comprising receiving third information associated with the at least one scan of the at least one live subject corresponding to an absence of the at least one effect of the at least one RF transmitting arrangement, and determining the second information based on the first information and the third information.

14. The computer-accessible medium of claim 1, wherein the computer arrangement is further configured to correct for main magnetic field changes in space in the first information.

15. A system comprising:
   a computer hardware arrangement configured to:
      a. activate the at least one RF transmitting arrangement while a scanner table of a magnetic resonance (MR) scanning arrangement which has at least one live subject thereon is located outside of a scanner bore of the MR scanning arrangement;
      b. cause a movement of the scanner table which has the at least one live subject thereon inside of the bore;
      c. receive a first information associated with at least one scan of at least one live subject provided on the scanner table inside the bore corresponding to at least one effect of at least one radio frequency transmitting arrangement on the at least one live subject; and
      d. determine a second information based on the first information.

16. The system of claim 15, wherein the at least one RF transmitting arrangement comprises at least one antenna placed within a scanning arrangement connected to at least one power arrangement placed at a particular distance from the scanning arrangement so as to not interfere with the scanning arrangement.

17. The system of claim 16, wherein the at least one antenna is connected to the at least one power arrangement using a low-loss cable.

18. The system of claim 16, wherein the at least one power arrangement is an external power amplifier.

19. The system of claim 15, wherein the computer hardware arrangement is further configured to correct for main magnetic field changes in space in the first information.

20. A method for evaluating at least one radio frequency (RF) transmitting arrangement, comprising:
   activating at least one RF transmitting arrangement while a scanner table of a magnetic resonance (MR) scanning arrangement which has at least one live subject thereon is located outside of a scanner bore of the MR scanning arrangement;

causing a movement of the scanner table which has the at least one live subject thereon inside of the bore;

receiving a first information associated with at least one scan of at least one live subject provided on the scanner table inside the bore corresponding to at least one effect of the at least one RF transmitting arrangement on the at least one live subject; and with a computer hardware arrangement, determining a second information based on the first information.

21. The method of claim 20, wherein the at least one RF transmitting arrangement comprises at least one antenna placed within a scanning arrangement connected to at least one power arrangement placed at a particular distance from the scanning arrangement so as to not interfere with the scanning arrangement.

22. The method of claim 21, wherein the at least one antenna is connected to the at least one power arrangement using a low-loss cable.

23. The method of claim 21, wherein the at least one power arrangement is an external power amplifier.

24. The method of claim 20, further comprising correcting for main magnetic field changes in space in the first information.

25. A system for evaluating at least one frequency emitting device, comprising:

a magnetic resonance (MR) scanning arrangement including a bore;

at least one antenna of the at least one frequency emitting device positioned outside of the bore;

a drive source arrangement connected to the at least one antenna, and configured to cause the at least one antenna to emit a radiation; and a computer hardware arrangement configured to:
  activate the at least one frequency emitting device while a scanner table of the MR scanning arrangement is located outside of the bore;
  cause a movement of the scanner table inside of the bore; and
  evaluate the at least one frequency emitting device using the MR scanning arrangement.

26. The system of claim 25, wherein the drive source arrangement includes a power supply.

27. The system of claim 25, further comprising a barrier arrangement configured or structured to at least one of reduce or eliminate an electro-magnetic radiation from being projected from the MR scanning arrangement.

28. The system of claim 27, wherein the barrier arrangement has a first side that is closest to the MR scanning arrangement and a second side which is opposite to and away from the MR scanning arrangement, wherein an amount of the electro-magnetic radiation is lower at the second side than at the first side, and wherein the drive source is connected to a frequency emitting device that is located on the first side of the barrier arrangement.

29. The system of claim 25, wherein the at least one frequency emitting device and the drive source arrangement are housed in a single housing.

* * * * *